United States Patent [19]

Thompson

[11] Patent Number: 4,993,268
[45] Date of Patent: Feb. 19, 1991

[54] METHOD OF TESTING A HONEYCOMB JOINING PIN AGAINST SEATING FAILURES

[75] Inventor: Kenneth W. Thompson, Clearwater, Fla.

[73] Assignee: ATR International, Inc., Clearwater, Fla.

[21] Appl. No.: 524,927

[22] Filed: May 16, 1990

[51] Int. Cl.⁵ .................................................. G01N 3/08
[52] U.S. Cl. .......................................... 73/827; 73/842
[58] Field of Search .................... 73/827, 150 A, 834, 73/842

[56] References Cited

U.S. PATENT DOCUMENTS 4,876,896 10/1989 Snow et al. ............................ 73/827

Primary Examiner—Jerry W. Myracle
Attorney, Agent, or Firm—Herbert W. Larson

[57] ABSTRACT

The test method employed uses a cylindrical solid aluminum pin having a first stem portion and a threaded second portion separated by a middle necked down portion. The test pin threaded portion is inserted into a flowable adhesive such as an epoxy inside a joining pin located in a hole through abutting honeycomb panels and the epoxy is allowed to cure. A force is exerted on the first portion of the test pin until either the test pin separates at the necked down portion or the test pin is dislodged from the joining pin. In the latter case, the test indicates an improper mixture or a poor curing of the adhesive.

7 Claims, 3 Drawing Sheets

METHOD OF TESTING A HONEYCOMB JOINING PIN AGAINST SEATING FAILURES

BACKGROUND OF THE INVENTION

1. Field of the Invention

This invention relates to methods of testing for honeycomb joining pin seating failures. More particularly it refers to a method of inserting a test pin into an epoxy adhesive to determine if a joining pin has been properly seated in a honeycomb panel.

2. Description of the Prior Art

U.S. Pat. No. 4,370,372 describes a pin for joining two composite honeycomb panels and a method for joining the honeycomb panels using the pin. The pin described in the patent has received widespread commercial acceptance for use in joining honeycomb panels, particularly those panels used in aircraft. The only problem encountered in the use of the pin is occasional improper mixing of the epoxy adhesive anchoring material or poor bonding of the pin. Heretofore, there has been no reliable, inexpensive method of testing for improper bonding. Related, testing procedures for determining adhesive strength of a thin film to a surface are described in U.S. Pat. Nos. 3,336,797 and 3,527,093. A device for measuring tack time is described in U.S. Pat. No. 4,312,212. U.S. Pat. No. 4,538,083 describes a method for testing the tensile strength and bonding strength of sprayed on foam insulation attached to fuel tanks. A reliable and inexpensive method of testing for proper bonding of a pin joining two honeycomb panels is needed.

SUMMARY OF THE INVENTION

I have discovered a quick, reliable and inexpensive method of testing a pin joining two honeycomb panels to see that it is bonded properly. My method is a nondestructive test for properly installed pins, but will produce failure in improperly installed pins.

The first step in my method is to join two abutting honeycomb panels with a joining pin such as set forth in U.S. Pat. No. 4,370,372, incorporated herein by reference. An adhesive such as an epoxy is injected into the joining pin selected for test. The test pin is inserted into the throat of the joining pin by pushing into the adhesive prior to setting until a necked down portion of the test pin is below the flare at the head of the joining pin. The epoxy is then allowed to cure. A test base is then placed over the test pin so that the test pin stem protrudes through the top of the test base. The test pin stem is then engaged with a pop-rivet hand gun and a tension load is exerted on the stem by cycling the handle of the rivet gun until either the stem breaks away at the necked down section or until the adhesive fails and the test pin is pulled loose from the honeycomb panel joining pin.

BRIEF DESCRIPTION OF THE DRAWINGS

The invention may be best understood by those having ordinary skill in the art by reference to the following detailed description when considered in conjunction with the accompanying drawings in which.

DETAILED DESCRIPTION OF THE INVENTION

Figure 1:
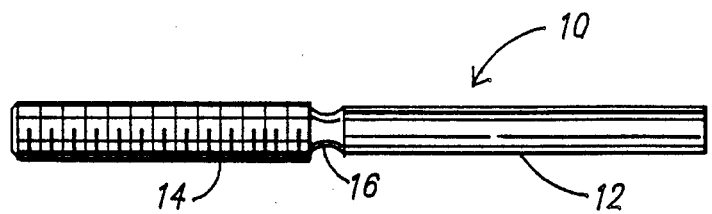
FIG. 1 is a side view of the test pin used in the method.

Throughout the following detailed description, the same reference numerals refer to the same elements in all figures.

Figure 2:
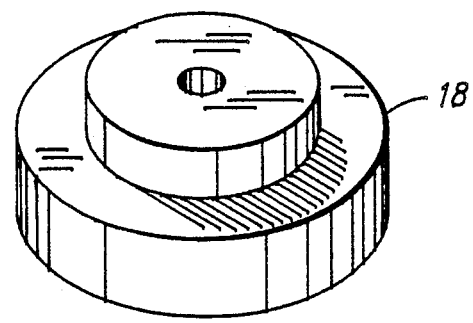
FIG. 2 is a perspective view of the test pin base.
Figure 3:
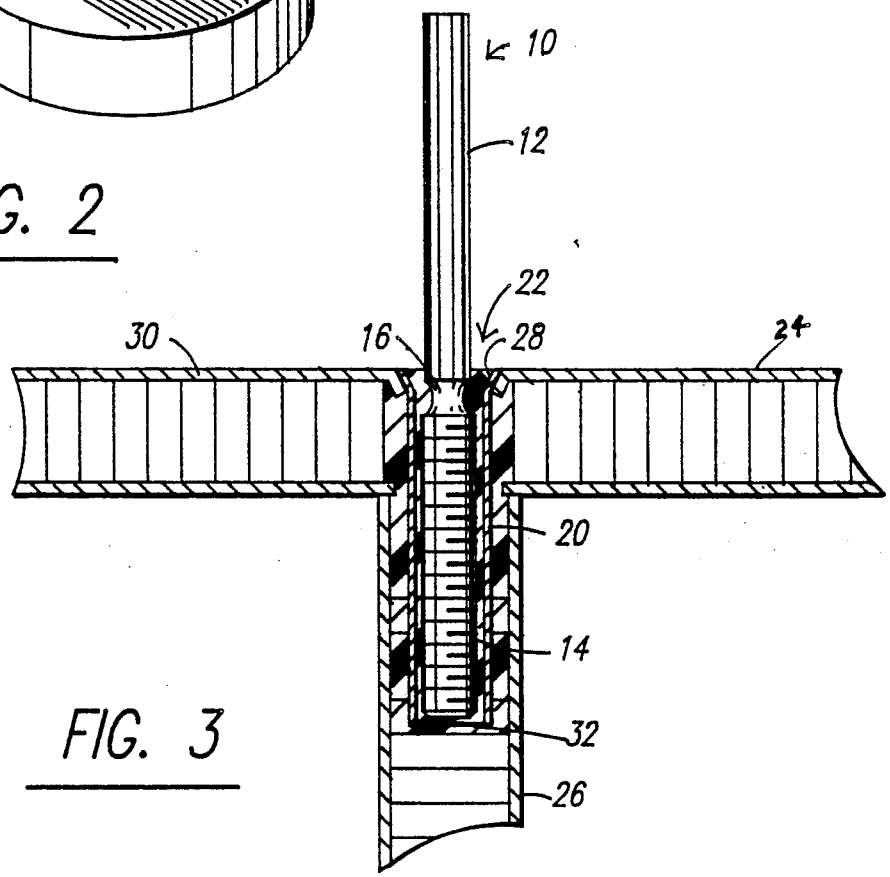
FIG. 3 is a cross section in elevation of the test pin centered in a joining pin prior to testing.

The test pin 10 used in the method of this invention has a first portion 12 having a smooth cylindrical contour and a second cylindrical portion 14 having multiple screw threads thereon. The first and second portions are separated by a necked down middle portion 16 as shown in FIG. 1. A base plate 18 shown in Figure 2 is one of the elements used in the method of this invention to support the test pin 10.

Figure 7:
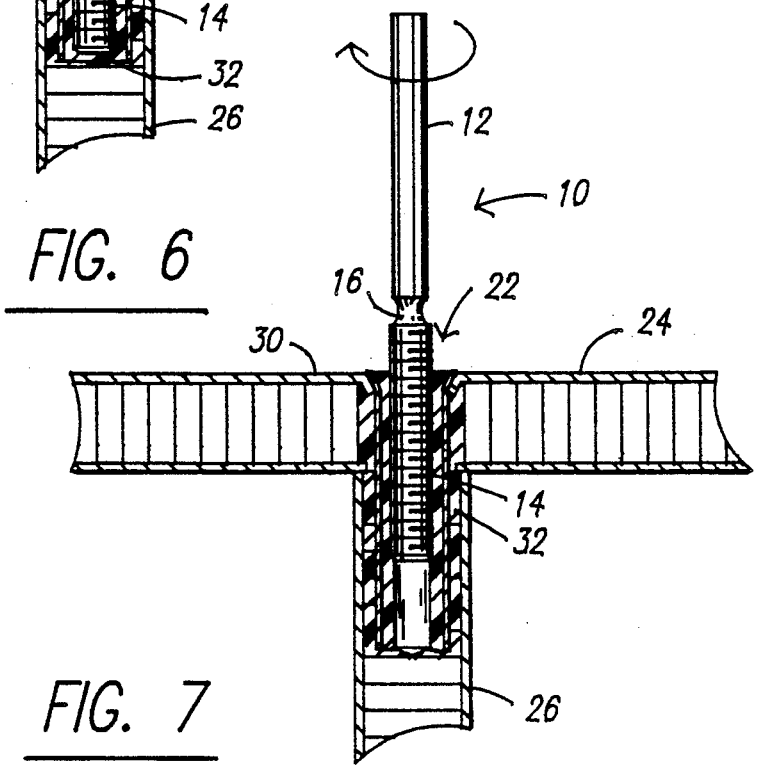
FIG. 7 is a cross section of the test pin being screwed into a drilled out center portion of a joining pin containing cured epoxy.

The joining pin 20, is first inserted into a hole 22, joining two honeycomb panels 24 and 26, respectfully. Flowable epoxy adhesive 32 of the right chemical mix is inserted into pin 20. Pin 20 is hollow in structure with multiple apertures in its tubular body as shown in U.S Pat. No. 4,370,372. Pin 10 is inserted into pin 20, so that the top portion of the neck 16 is approximately even with the flare 28 of pin 20 which is flush with the top surface 30 of honeycomb panel 24. Alternatively, the epoxy material 32 can be inserted into the pin 20 and then allowed to cure. Thereafter, the epoxy adhesive is drilled out so that the test pin 10 threads 14 can be screwed into the epoxy as shown in FIG. 7. Either method of inserting the test pin is acceptable.

Figures 4, 5:
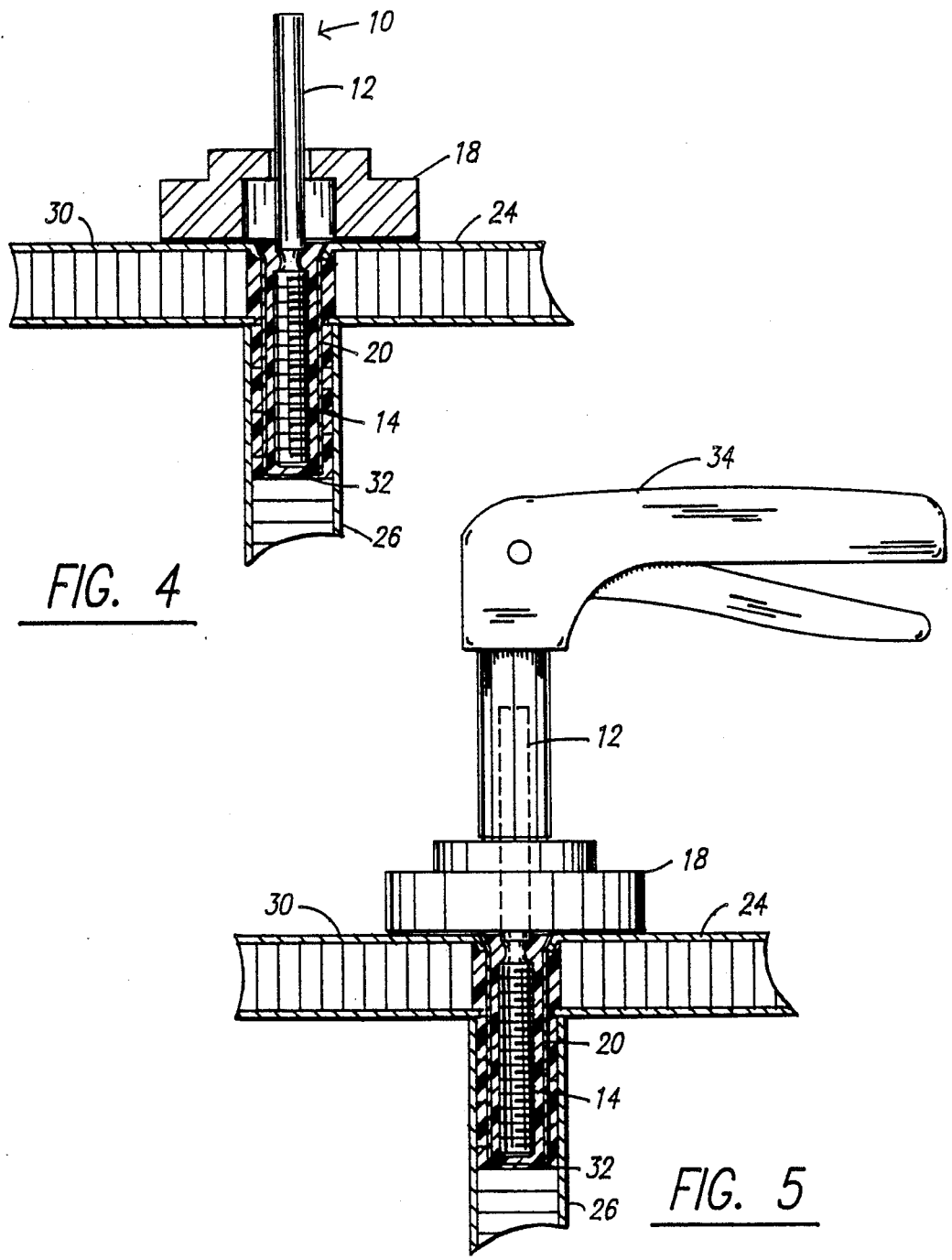
FIG. 4 is a cross section in elevation of the test pin inserted through the test base of FIG. 2 and centered in a joining pin holding two adjacent honeycomb panels together.
FIG. 5 is a cross section of the test pin inserted with epoxy adhesive and grasped by a pop-rivet hand gun.

Thereafter, the base plate 18 is inserted over the top portion 12 of the test pin 10, so that it rests on the top surface 30 of the honeycomb panel as seen in FIG. 4.

Figure 6:
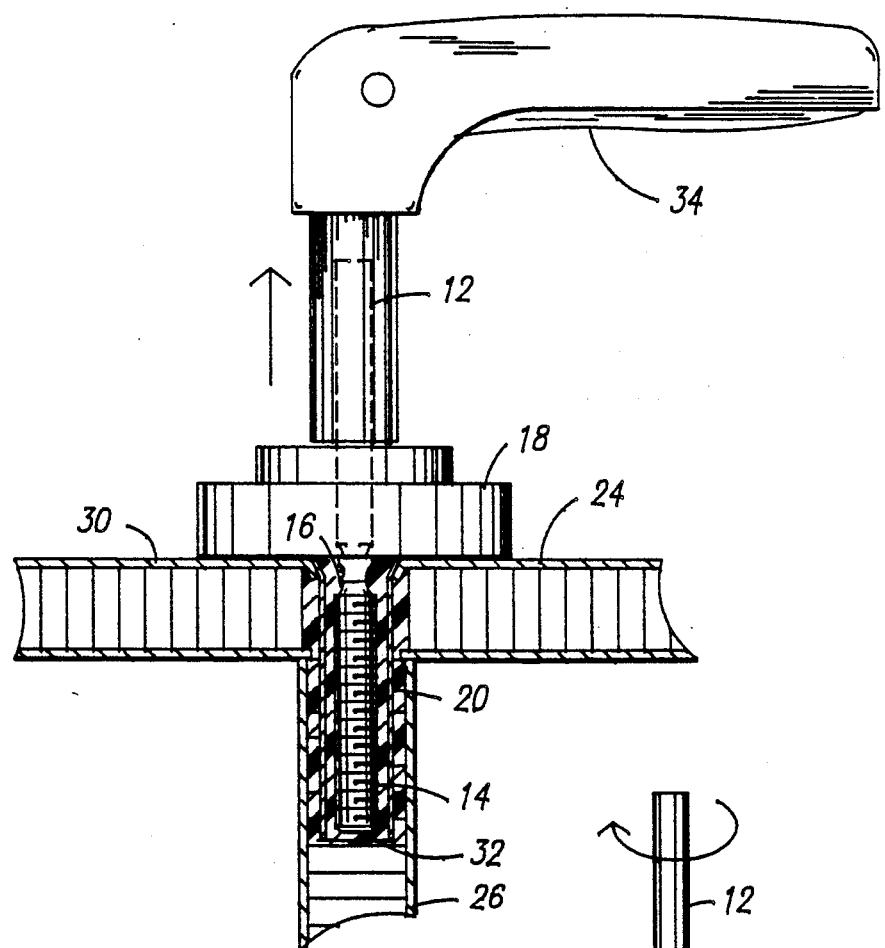
FIG. 6 is a cross section showing the pop-rivet hand gun breaking the test pin at its neck.

The test pin first portion 12 is then rotated with a tool 34 such as a pop-rivet hand gun device. The handle of the pop-rivet hand gun 34 is cycled until either the neck 16 of the test pin fails in tension as seen in FIG. 6 or the test pin is partially or fully dislodged from the honeycomb panel joining pin 20.

The test pin 10 is preferably made of aluminum. Commercial 6061-T6 extruded rod aluminum alloy has been found to be most preferred. Such a pin 10 is pulled in tension by the pop-rivet gun to either break the pin 10 at the neck 16 or as stated above dislodge the pin 10 from the honeycomb joining pin 10. Using a 0.030 inch radius neck portion on a stem 0.110 inches in diameter and a 3.25 inches long pin, a force of 145 pounds is sufficient to break the pin at its neck if the epoxy adhesive is properly mixed and cured. If the pin does not break, but instead pulls loose from the epoxy, then the epoxy mixture or the curing process is defective.

The type of adhesive used can vary as known in the industry, but a preferred one for joining pins as set forth herein is an epoxy such as commercial ATR 525 A/B. Other materials can be substituted for the aluminum in the test pin 10 and other adhesives can be substituted. The base plate 18 is made from a high strength aluminum metal alloy which is sufficiently strong to withstand the pressures exerted by the pop-rivet gun.

Having thus described the invention, what is claimed and desired to be secured by Letters Patent is:

1. A method of testing the seating strength of a joining pin connecting two honeycomb panels comprising inserting into the joining pin filled with an adhesive a substantially cylindrical solid test pin having a necked down middle portion separating a first stem portion and a threaded second portion, the necked down portion of the test pin being located adjacent to a flare at a head of the joining pin, ensuring that the test pin second portion is firmly seated in the adhesive, and pulling the test pin at the first portion with a tool to exert a force on the test pin until either the test pin separates at the necked down portion or the test pin is dislodged from the honeycomb panel joining pin.

2. A method according to claim 1 wherein the test pin second portion is inserted into an adhesive in a flowable stage and the adhesive is allowed to cure around the threaded portion of the test pin.

3. A method according to claim 1 wherein cured adhesive is drilled out to form a receptacle for the threaded second portion of the test pin and the test pin is screwed into the adhesive.

4. A method according to claim 1 wherein the test pin is made from aluminum.

5. A method according to claim 4 wherein a pulling force of at least 145 pounds is exerted on the test pin first portion while the second portion is imbedded in an epoxy adhesive.

6. A method according to claim 1 wherein the adhesive is an epoxy.

7. A method according to claim 1 wherein the tool is a pop-rivet hand gun.

* * * * *